United States Patent [19]

Charm et al.

[11] Patent Number: 5,539,673
[45] Date of Patent: *Jul. 23, 1996

[54] NON-INVASIVE INFRARED TEMPERATURE SENSOR, SYSTEM AND METHOD

[75] Inventors: Stanley E. Charm, Boston; Steven Landau, Brookline; Hossein Zarrineghbal, Winchester; Robert F. Golden, Acton, all of Mass.

[73] Assignee: Charm Sciences, Inc., Malden, Mass.

[*] Notice: The term of this patent shall not extend beyond the expiration date of Pat. No. 5,389,335.

[21] Appl. No.: 317,169

[22] Filed: Oct. 3, 1994

Related U.S. Application Data

[63] Continuation of Ser. No. 79,680, Jun. 18, 1993, Pat. No. 5,389,335.

[51] Int. Cl.⁶ .................................................. G01J 5/00
[52] U.S. Cl. ................. 364/557; 422/82.12; 426/521; 219/679; 219/711; 210/742; 73/61.48; 356/44; 374/121; 374/131; 374/141
[58] Field of Search .................................. 364/550, 557; 422/21, 307, 82.11, 82.12; 426/241, 520, 521, 522; 219/678, 679, 687, 689, 711; 210/742, 748; 73/61.46, 61.48; 250/338.1, 339.03, 339.04, 341.8, 343, 346; 356/43, 44, 51; 374/120, 121, 131, 132, 141

[56] References Cited

U.S. PATENT DOCUMENTS

| 4,203,326 | 5/1980 | Gottlieb et al. | 374/162 |
|-----------|--------|-----------------|---------|
| 4,737,038 | 4/1988 | Dostoomian | 374/139 |
| 4,975,246 | 12/1990 | Charm | 422/21 |
| 5,145,257 | 9/1992 | Bryant et al. | 374/131 |
| 5,288,471 | 2/1994 | Corner | 422/307 |

Primary Examiner—Emanuel T. Voeltz
Assistant Examiner—Edward Pipala
Attorney, Agent, or Firm—Richard P. Crowley

[57] ABSTRACT

A high temperature, short time microwave heating system 10 for heat-sensitive liquid material to inactivate or reduce pathogenic agents or organisms, such as viral contaminants. The system 10 includes a disposable cartridge 26 consisting of a preheater 32, a microwave heating coil 56 and cooler 58 with the heating coil 56 adapted to be easily inserted in and removed from the microwave heating field.

21 Claims, 3 Drawing Sheets

NON-INVASIVE INFRARED TEMPERATURE SENSOR, SYSTEM AND METHOD

This is a continuation of application Ser. No. 08/079,680 filed on Jun. 18, 1993 now U.S. Pat. No. 5,389,335.

BACKGROUND OF THE INVENTION

It is desirable to sterilize, pasteurize or otherwise heat treat heat-sensitive material by heating such heat-sensitive material, such as biological fluids, to high temperatures for very short time periods without affecting substantially the other desirable properties of the heat-sensitive material. U.S. Pat. No. 4,839,142, issued Jun. 13, 1989 and U.S. Pat. No. 4,975,246, issued Dec. 4, 1990, both disclose high temperature, short time heating systems and methods for the heating of heat-sensitive material to destroy substantially the pathogenic or other microorganisms, such as viruses, in the heat-sensitive material without substantially affecting other desirable properties of the heat-sensitive material, such as proteinaceous matter.

These patents disclose a system and method in which heat-sensitive material, such as a biological fluid, such as blood plasma or serum or tissue culture or tissue-type or other material, is rapidly heated by microwave energy to a selected temperature, held for a very short holding time and then rapidly cooled and then recovered. Typically, the method described provides for rapidly heating the heat-sensitive material at a rate of over 50° C. per second, for example 50° C. to 2000° C. per second, for a heating time period typically less than one second to a preselected temperature of typically over about 60° C. and to a temperature wherein the rate of reduction or destruction of the pathogenic organisms is greater than the rate of destruction of the heat-sensitive material by employing microwave energy to accomplish the rapid heating. The method includes holding the heated heat-sensitive material at a preselected temperature for a short holding time period which might be quite short, for example less than 0.05 seconds, and then rapidly cooling the heated heat-sensitive material to a preselected lower temperature, typically less than about 40° C., or typically less than 30° C., in a short time period to provide a cooled heat-sensitive material with the virus or agent destroyed or reduced. The heat-sensitive material is rapidly heated and rapidly cooled, while circulating the heat-sensitive material through a plastic tubing, with the total heating, holding and cooling time periods not greater than 1.0 seconds and sufficiently short so as not to substantially effect the desirable properties, such as the Factor VIII and IX properties of blood plasma or serum, but sufficient for the desirable reduction of the pathogenic organisms, viruses or microorganisms in the heat-sensitive material, typically to effect a multilog, e.g. six-log or more, cycle reduction of the microorganism.

It is desirable to provide for a new, efficient, controlled batch and continuous system and method for the high temperature, short time heating for heat-sensitive material which overcomes at least some of the disadvantages in the prior high temperature, short time heating system and method.

SUMMARY OF THE INVENTION

The invention relates to a high temperature, short time heating system and method and in particular, to a high temperature, short time heating system and method for heat-sensitive material which will preserve the selected biological characteristics of the heat-sensitive material, while achieving multilog reductions of pathogenic agents, such as viruses, in the heat-sensitive material.

The high temperature, short time heating system of the invention is directed to heat-sensitive material, particularly biological fluids, which system comprises a microwave wave guide to provide microwave energy to the heat-sensitive fluid, typically a liquid, to be treated, and microwave power supply to supply electrical power to the microwave wave guide. The system includes computer and electronic controls optionally with a display screen and optionally with a printer to provide for control of the process parameters of the high temperature, short time heating system, such as the preheating, heating and cooling times and temperatures of the heat-sensitive material. The system includes a pump or pump means to pump the heat-sensitive fluid through the system and a feed source, or feed container, for the heat-sensitive fluid to be treated, and a collection source for the collection of the sterilized, pasteurized or heat-treated fluid after passing through the system.

The system also includes a cartridge, typically in the preferred embodiment, a disposable, easily inserted and removable cartridge which provides a movable sanitary system with disposable contact parts for simple cleaning and sterilization, particularly for use with blood plasma, serum and with tissue cultures and other sanitary, sensitive-type material. The cartridge includes a preheater composed of a housing and containing a plurality of tubing in the housing for the passage of the fluid to be preheated and treated therethrough, and an inlet and an outlet for the introduction and withdrawal of hot water to provide for preheating of the fluid in the tubing. The cartridge would also include a microwave heating coil containing a plastic or non-microwave susceptible material holder and plastic tubing susceptible to the passage of microwave energy, such as flexible, transparent plastic tubing, to permit the rapid microwave heating of the preheated fluid passing through the tubing, the microwave heating coil positioned to form uniform generally parallel loops and positioned within the microwave field of the microwave guide and adapted to be inserted within an opening in the microwave guide and into the microwave heating field.

The cartridge includes a cooler containing a housing with a plurality of coils of tubing to receive the microwave heated fluid and an inlet and outlet for the introduction and withdrawal of cold water in the housing to cool rapidly the microwave heated fluid to a temperature generally less than 40° C. in a time of less than about 1.0 second, and preferably less than about 0.5 seconds. The cartridge typically would include metal tubing in the preheater and the cooler, such as stainless steel tubing, and include flexible, microwave transparent plastic tubing, such as a fluorocarbon tubing, like Teflon® tubing, typically transparent, connected to the metal tubing of the preheater and between the outlet of the preheater and the inlet of the cooler and with other tubing means to connect the feed source, the pump, the cartridge and the collection means to permit the pumped passage of the fluids from the feed source by the pump through the cartridge means and into the collection means.

The cooler may be mounted on a bracket which is in turn mounted to an adjustable screw. As the screw is adjusted the cooler moves up or down, drawing an amount of tubing out of the microwave field. The portion of the tubing between the microwave field and the cooler holds the microwave heated fluid at a relatively constant temperature for a period of time (the hold time) prior to cooling. The hold time is proportional to the velocity of the fluid in the tubing and the length of the tube between the microwave field and the cooler. By adjusting the length of this tubing the hold time can be adjusted without changing the flow rate of the heat sensitive fluid.

The microwave heating coil used comprises a plurality of loops of the plastic tubing of defined length, within a plastic coil retaining holder means to retain the plastic tubing in a generally parallel, uniform, side by side, slightly spaced apart, coiled arrangement of the plastic tubing which may be easily positioned within the microwave guide. The plastic coil retainer or holder may comprise a base portion and a downwardly extending holder of a plastic material adapted to extend through an opening in the microwave guide, housing and into the microwave heating field and having a plurality of spaced apart, side by side slots or holes through which the microwave plastic tubing may be threaded, and generally with a plurality of aligned upper and lower holes to thread the tubing therefrom and to hold the plastic tubing in the arranged, coiled manner. The cartridge with the preheater, the microwave coil and the cooler should generally be arranged in one preferred embodiment so that the entire unit may be disposable, and typically would comprise a base with the preheater and the cooler on the upper surface of the base and the microwave heating coil extending below the base for use in the microwave guide energy field. The employment of a disposable cartridge is particularly preferred and adaptable with culture media, plasma material or other type material where the cartridge must be cleaned between each use.

The microwave heating coil may be mounted on a fixed frame or a rotatable grooved spindle. When the cooler is adjusted, sufficient slack tubing is provided to allow the cooler to pull out the required length of tubing when adjusted. If the tubing is mounted on a rotatable spindle, when the cooler is adjusted the spindle rotates thus feeding tubing to the cooler and drawing tubing from slack supplied between the preheater and the microwave field.

Generally, the disposable cartridge employed in sterilizing or pasteurization operations comprises a combination of a preheater-type heat exchanger, a coiled microwave tube and a cooling heat exchanger with a continuous tube constructed of lengths of metal and plastic material passing through the cartridge, the metal tubing material being used in the preheater and the cooler, while the plastic tubing material is used in the microwave coil guide. In operation, the heat-sensitive fluids are passed through this tubing which runs through the preheater, the microwave field and the cooler, with the flexible plastic tube of defined length and diameter and coiled in the microwave coil guide to provide satisfactory exposure to the microwave energy and to raise rapidly, e.g., less than 200 milliseconds, the heat-sensitive fluid to the high appropriate temperatures, e.g. over 60° C., such as 70° C. to 180° C., within the short time period desired, e.g. 5 milliseconds. The tube diameter, the length and the number of coils in the microwave field, may be varied as desired.

The computer electronic control employed in the process merely operates on an algorithm for the control of the process for microwave sterilizing, pasteurizing or otherwise heat-treating the heat-sensitive fluid, and which accepts real time inputs from pressure, flow, temperature, motor and other sensors in the system and employs this information to control the time-temperature history of the heat-sensitive fluid flowing through the flexible plastic tubing which is coiled through the microwave field.

The system optionally and preferably includes the accurate sensing of the fluid temperature in the inlet and outlet of the microwave coiled plastic tubing and in particular, employs with transparent tubing a non-invasive IR infrared sensor employing an IR sensor in conjunction with fiber optic cable in which an infrared sensor or fiber optic cable is coupled to an IR sensor placed in physical contact with and adjacent to the microwave plastic tube in which the heat-sensitive material is flowing in and out of the microwave coil. Generally, the signal from the IR sensors is amplified and then sent into the computer electronic control to act as one of the process parameters.

The system of the invention may be used with a wide variety of fluids to be sterilized, pasteurized or heat treated, which would include heat-sensitive liquids, such as biological liquids, solutions, suspensions and the like, and would include, but not be limited to, blood and serum, plasma, cell culture media and the like, and in particular, heat-sensitive material which contains HIV (human immunodeficiency virus), EMC (encephalo myocardia virus) and unknown viruses which can cause a major problem in such a heat-sensitive material. The system permits viral inactivation of a heat-sensitive material either in batch form or in a continuous operation. The system avoids the difficulties associated with other systems and methods, for example, conventional thermal methods which tend to destroy delicate biological materials and the use of filters which clog with cell culture media or blood products, or conventional chemical methods which add substances are difficult to remove or otherwise effect the fluid.

The system permits the high temperature, short time heating of fluid, for example in less than 0.1 seconds, for example, less than 0.05 seconds, such as 0.01 seconds. The system permits a total heating, holding and cooling time of less than about one second, with heating and cooling total times of only a few milliseconds, typically 500 to 200 milliseconds or less.

The invention will be described for the purposes of illustration only in connection with certain embodiments; however, it is recognized that various changes, additions and improvements can be made in the invention by those persons skilled in the art, all falling within the spirit and scope of the invention.

DESCRIPTION OF THE PREFERRED EMBODIMENTS

Figure 1:
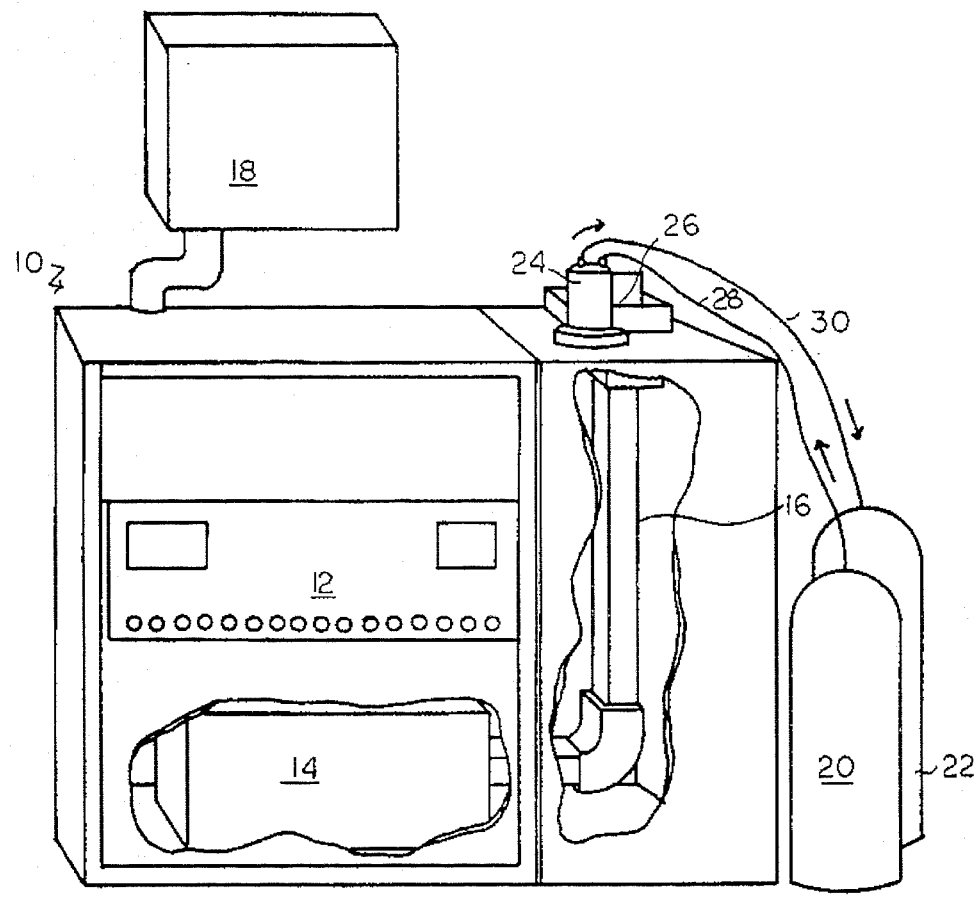
FIG. 1 is perspective view of the high temperature, short time microwave heating and cooling system of the invention.

FIG. 1 shows the high temperature, short time microwave heating system 10 of the invention which comprises computer electronics controls 12 to monitor the parameters of the high temperature, short time process which includes a computer display 18 and which system includes a microwave power supply 14 which supplies microwave power to microwave guide 16. The system includes a feed tank 20 to supply a heat-sensitive material to be treated and a collection tank 22 for the recovery of the sterilized, viral inactivated or heat processed heat-sensitive material and which includes a pump 24 connected through tubing 28 and 30 and a disposable cartridge 26, the disposable cartridge shown in more detail in FIG. 2, and which is disposably placed over and within an opening at the end of the wave guide 16, so that the portion of the disposable cartridge 26 comprising the microwave coil is disposed in the microwave energy field.

Figure 2:
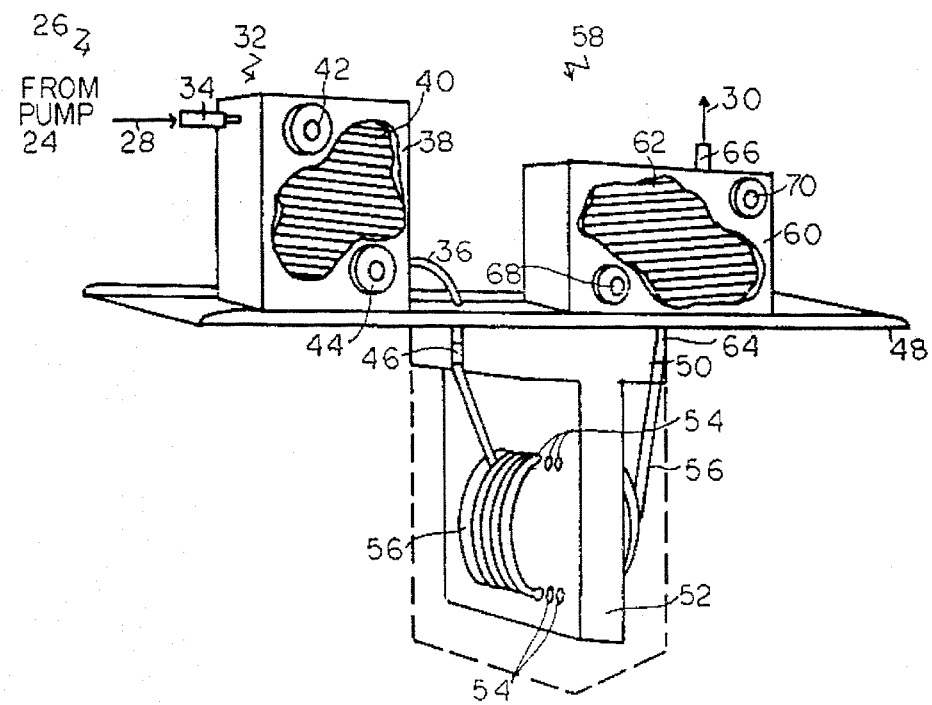
FIG. 2 is a perspective, schematic, enlarged illustration of the disposable cartridge system used in the system of FIG. 1.

FIG. 2 is a perspective view of a disposable cartridge 26 for use with the system 10 in FIG. 1 which cartridge has a preheater 32 containing a inlet 34 for the introduction of a heat-sensitive material from a pump 24 to be treated, the preheater comprising a transparent plastic housing 38 containing a plurality of coils of stainless steel metal 40 therein and having an outlet 36 which connects to a metal or plastic tubing 46 connection wherein the housing 38 has an inlet 42 for the introduction of hot water, for example, 70° C. to 95° C., and more particularly 80° C. to 85° C., and an outlet 44 for the withdrawal of the hot water after preheating the heat-sensitive fluid in the coil 40.

The disposable cartridge 26 includes a plastic, T-shaped microwave coil holder having a base 50 and a downwardly extending portion 52, the base 50 extending to and secured to the bottom of a base 48 on which the preheater 32 and a cooler 58 are positioned, the base 50 being rectangular and adapted to fit into the opening at the end of the microwave guide 16. The holder extension 52 includes a plurality of spaced apart, aligned holes 54 in the upper and lower sections of the holder and includes a plastic tubing 56, such as, but not limited to, a Teflon® tubing, of a desired diameter, such as 1/16 to 1/2 inch, sequentially wound or threaded through the holes 54 to form a plurality of side-by-side, generally uniform, spaced apart coils which are to be placed in the microwave field, the diameter of the tubing and the number of coils with the pumping rate selected to provide for the desired exposures and for the rapid heating of the heat-sensitive material within the coils 56. The plastic coil 56 is secured by being threadably turned onto threads at the end of the stainless steel outlet 46 from the preheater 32.

The disposable cartridge 26 also includes on the upper portion of the base 48 a cooler 58 which comprises a transparent plastic housing 60 having a plurality of coils of stainless steel tubing 62 therein and having an inlet 64 which is threadably connected to the plastic tubing 56 from the microwave coil 50, and an outlet 66 in the transparent housing 60 which includes an inlet 68 for the introduction of cold water, and an outlet 70 for the withdrawal of cold water, the cold water being typically less than 10° C., for example, 2° C. to 10° C., where the total system is arranged, for example for 100 liters per hour of treatment of a heat-sensitive fluid, and the outlet tubing also selected so as to provide for a flow rate of 100 milliliters per second of heating and cooling the water. The flexible plastic tubing 56 employed in the microwave cooling guide may vary in length and diameter and in composition, but may comprise Teflon®, polyethylene, PVC or other tubing. However, it is preferable that the tubing be transparent, particularly when employed with the optical fiber IR sensor temperature system. The disposable cartridge 26 as designed and shown in FIG. 2 is designed to be inexpensive and disposable, so that the need for cleaning and sterilization of the tubing after each use is dispensed with and which is particularly useful for the treatment of blood plasma and serum or tissue cultures.

Figure 3:
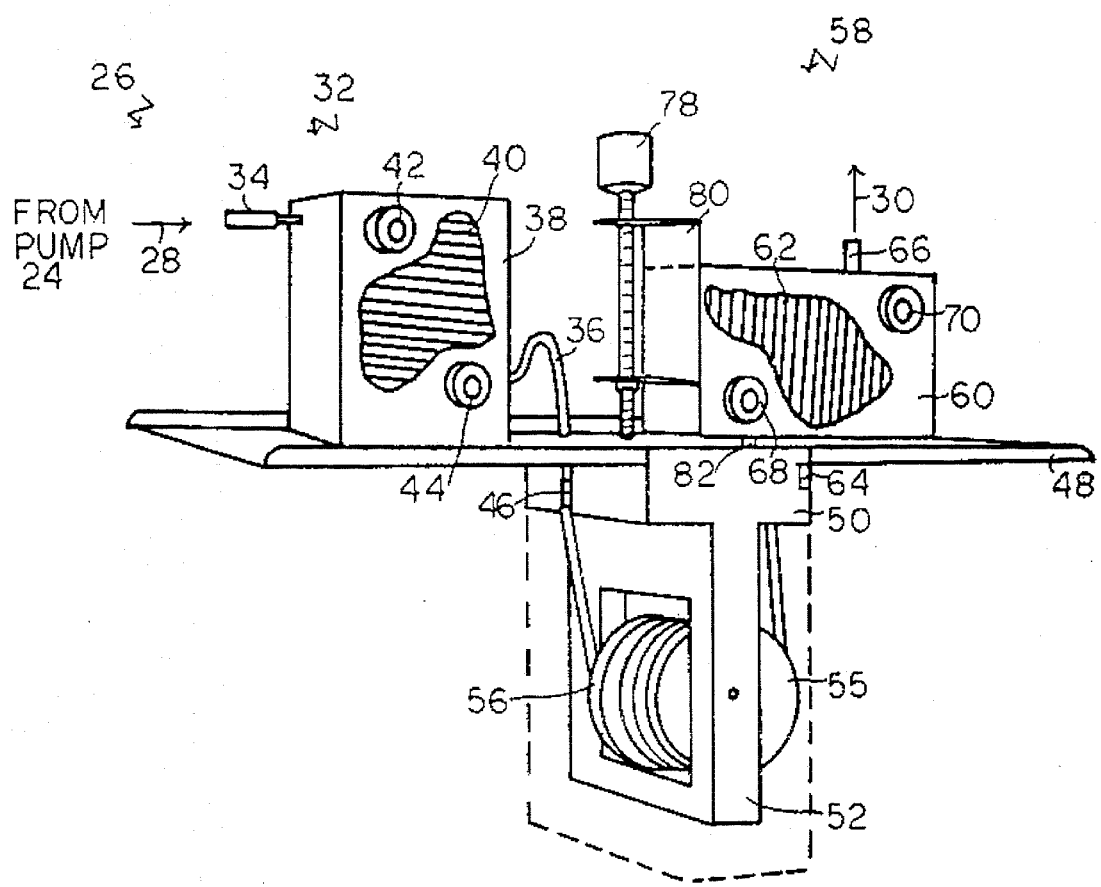
FIG. 3 is a perspective, schematic illustration of an alternative disposable cartridge system used in the system of FIG. 1.

FIG. 3 is a perspective of an alternative disposable cartridge 26 for use with the system 10 in FIG. 1 which cartridge consists of a preheater 32 containing an inlet 34 for the introduction of a heat-sensitive material from a pump 24, the preheater comprising a transparent plastic housing 38 containing a plurality of coils of stainless steel metal tubing 40 therein which connects to plastic tubing 36 which has sufficient length or slack to allow adjustment of the cooler 58 and is supported to facilitate movement in and out of the microwave field. The housing 38 has an inlet 42 for the introduction of hot water or other fluids, for example 50° C. to 100° C., and more particularly 80° C. to 85° C., and an outlet 44 for the withdrawal of the hot water after preheating the heat sensitive fluid in the coil The disposable cartridge 26 in FIG. 3 includes a plastic frame extension 52 which holds a plastic spindle coil holder 55 grooved to hold the coils in the desired spacing. The frame 52 has a base 50 extending to and secured to the bottom of a base 48 on which the preheater 32 and a cooler 58 are positioned, the base being rectangular and adapted to fit into the opening at the end of the microwave guide 16. The spindle coil holder 55 holds sequential coils of plastic tubing and can turn in the frame 52 when the cooler 58 is adjusted with the cooler adjustment screw 78. The spindle 54 holds the tubing coil 56 such as, but not limited to, a Teflon® tubing, of a desired diameter, such as 1/16 to 1/2 inch, sequentially wound on the spindle 55 to form a plurality of side-by-side, generally uniform, spaced apart coils which are to be placed in the microwave field, the diameter of the tubing and the number of coils with the pumping and cooler adjustment are selected to provide for the desired exposures and for the rapid heating of the heat-sensitive material within the coils 56. The plastic coil 56 is secured by being wound into threads at the end of the stainless steel coil 40 in the preheater 32.

The disposable cartridge 26 in FIG. 3 also includes on the upper portion of the base 48 a cooler 58 which comprises a transparent plastic housing 60, mounted on a bracket 80 which can be adjusted up or down using screw 78 thus extending the length of plastic tubing 82 outside of the microwave field and prior to the cooler which determines the time at which the heat sensitive fluid is held at the desired temperature and having a plurality of coils of stainless steel tubing 62 therein and having an inlet 64 which is threadably connected to the end of the plastic tubing 56 making up the microwave coil, and an outlet 66 in the transparent housing 60 which includes an inlet 68 for the introduction of cold water or other coolant, and an outlet 70 for the withdrawal of cold water or coolant, the cold water being typically less than 100° C., for example, 2° C. to 10° C., where the total system is arranged for example for 10 liters per hour of treatment of a heat sensitive fluid, and the outlet tubing also selected so as to provide for a flow rate of 100 milliliters per second of preheating fluid and coolant.

In operation, the disposable cartridge 26 (as in FIG. 2 or 3) is used by merely inserting the base 50 and extension holder 52 with the coiled up tubing 56 into the top rectangular open space of the housing of the microwave guide 16 in system 10, so that the base 48 rests on the top portion of the system 10 of the housing of the wave guide while the extensions 50 and 52 with tubing 56 is then placed in the microwave energy field of the wave guide 16. If an adjustable cartridge such as that in FIG. 3 is used, the screw 78 (FIG. 3) is then adjusted to achieve the desired hold time.

The tubing 28 is then connected to the inlet 34 and the tubing 30 connected to the outlet 66. After the sterilizing, pasteurizing or heat treatment of the heat-sensitive fluid, the disposable cartridge 26 may then be disconnected and lifted out and discarded, and a new cartridge 26 then inserted in the opening at the top of the wave guide 16 of the system 10.

Figure 4:
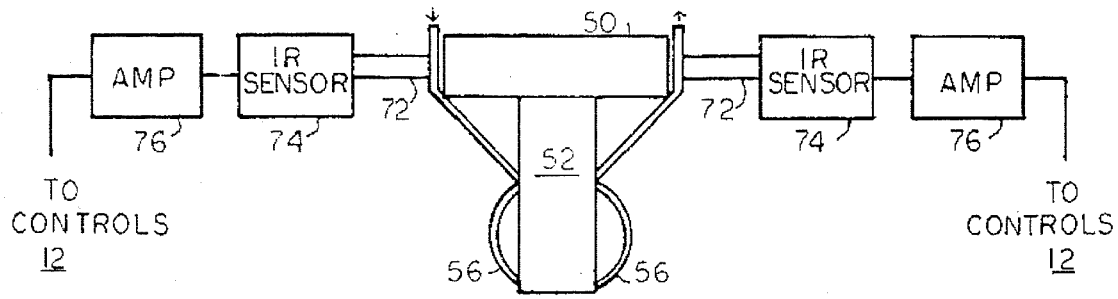
FIG. 4 is a schematic illustration of the infrared fiber optic, temperature sensing system used with the microwave heating coil shown in FIG. 2

FIG. 4 is a schematic plan view of the infrared fiber optic temperature sensor a portion of the system 10. The IR temperature sensor system is adapted for use wherein the tubing 56 is transparent and provides for a non-invasive technique for the accurate measurement of the inlet and outlet temperature into the microwave heating coil 56, which includes as illustrated a plurality of optical glass fibers placed together within an outer cable form 72 with the end of the optical fibers adjacent the outer transparent surface 56 on the inlet and outlet side of the microwave heating coil 56 and with the fibers adapted to collect and forward to an infrared sensor 74 the infrared heat of the fluid flowing in the tubing 56, to be converted into a temperature signal and the electrical signal amplified by an amplifier 76 and then returned to controls 12 contained in the monitoring system 10.

The IR sensor 74, in conjunction with the optical fiber 72, provides for an accurate, non-invasive technique for accurate measurement of the temperature of the heat-sensitive fluid at the inlet and outlet of the coil 56. In one embodiment, the tubing 56 would comprise a Teflon® tubing of ⅛ inch outside diameter and 1/16 inch inside diameter and is of an IR transparent material. The standard optical fibers for example may be made of zirconium fluoride glass having a diameter of about 100 microns and wherein the fibers may be arranged in multiple rows, such as two parallel rows to the tubing 56 against which they are placed. The number of optical fibers to be used may vary, but generally from 10 to 100 fibers, e.g. 20 to 50, would typically be employed with the fiber optic fibers placed within a fiber optic cable 72 terminated with a standard SMA connector, and then thereafter coupled with any brand of an IR sensor 74 and amplified. The IR sensor, for example, may be, but is not limited to, the Williamson Fiber View 6000, fiber optics single wave length, 4-wire, non-contact temperature transmitter and control system manufactured by Williamson Corporation of Concord, Mass., or similar infrared control system. Generally, the selection of IR sensor may differ depending upon the inlet or outlet temperature, the IR sensor typically being a broad band of 1–4 microns and selected, for example, to measure the inlet temperature to the tubing 56 which would be from 45° C. to 65° C., and the outlet temperature ranging from about 70° C. to 110°C. The end of the fiber optics is placed adjacent to the wall of the transparent tubing 56 and should be small enough to have an acceptable angle of acceptance in contact with the wall of the tubing 56.

Figure 5:
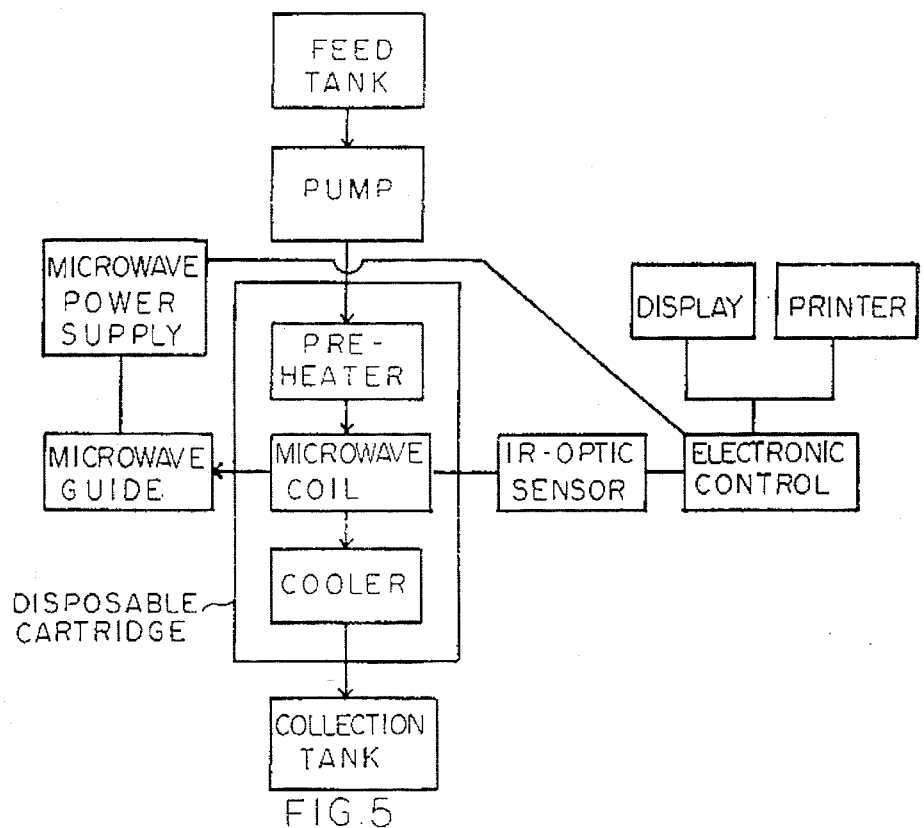
FIG. 5 is a schematic illustration of a block flow diagram of the components of the system of the invention.

FIG. 5 is a block-flow schematic diagram illustrating the system 10 of FIG. 1 in block-flow form.

Figure 6:
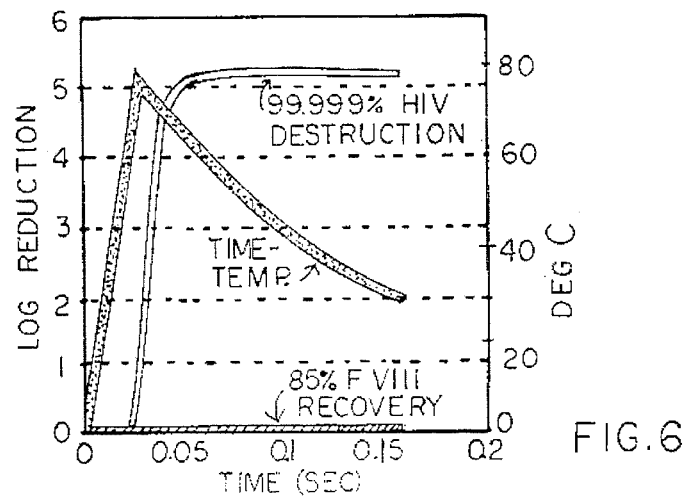
FIG. 6 is a graphical illustration of a high temperature, short time example of the viral inactivation of HIV in a blood plasma employing the system of FIG. 1 and recovering a heat-sensitive material Factor VIII using the system of FIG. 1.

FIG. 6 is a graphical illustration of an example of viral inactivation of HIV virus in blood plasma and recovery of the heat-sensitive viral inactive blood plasma employing the system 10 of the invention wherein the heat-sensitive material comprises a blood plasma and wherein the length of the tubing in the preheater 40 is about four feet and the length of the tubing in cooler 62 is about four feet, and wherein ⅛ inch Teflon® tubing 56 employed is about two feet in length and the holder 52 with the preheat inlet temperature to the microwave heating coil is 50° C. The graphical illustration shows an abscissa set forth in time (seconds) and an ordinate both in log reduction and degrees Centigrade and illustrates the rapid heating of the blood plasma to about 75° C. and the rapid cooling in a timed period of 0.02 seconds and a rapid cooling of about 0.2 seconds to a low temperature of 30° C. and the substantial destruction of 99.999% of the HIV virus with a recovery of the blood plasma of 85% of the F-VIII factor.

The described and illustrated system for the high temperature, short time heating of a material permits batch and continuous operation and employs preferably a disposable cartridge for use with materials which require a sanitary-type system and thus avoids frequent cleaning and sterilization, and yet, the system preserves the biological characteristics of the heat-sensitive material while achieving multilog reductions in pathogenic organisms.

What is claimed is:

1. A non-invasive, infrared system for the remote temperature measurement of a fluid in an apparatus, which system comprises:
 a) an apparatus containing a heated fluid and which includes an infrared energy transparent section to confine the heated fluid and having an interior surface and an exterior surface; and
 b) an infrared temperature sensor means which comprises:
  i) optical fiber means to collect and transmit infrared energy from the heated fluid and having a one and other end, which means at the one end is positioned non-invasively adjacent to the exterior surface of the said section, and in an infrared energy recovery position;
  ii) an infrared sensor means to receive from the other end the collected and transmitted infrared energy of the heated fluid to provide a sensing signal; and
  iii) means to receive and convert the sensing signal to a measure of the temperature of the heated fluid in the apparatus.

2. The system of claim 1 wherein the apparatus comprises a heat exchanger for a heat-sensitive liquid and the infrared transparent section includes a transparent tube.

3. The system of claim 1 wherein the transparent section comprises a flexible, coiled, fluoro-polymer tube.

4. The system of claim 1 wherein the apparatus comprises a means to heat the fluid and a coil of a transparent polymer tube having an inlet for the introduction of a fluid to be heated and an outlet for the withdrawal of a heated fluid and wherein the means to collect and transmit of the temperature sensor means is positioned at the one end adjacent the inlet, outlet or both the inlet and outlet of the tube.

5. The system of claim 4 wherein the heating apparatus includes a housing and the means to heat the fluid includes a microwave guide means in the housing to provide a microwave energy field and the said coil is positioned in the microwave energy field to heat the fluid in said tube.

6. The system of claim 1 wherein the optical fiber means to collect and transmit infrared energy from the heated fluid comprises a plurality of optical fibers within an outer cable, the optical fibers having an inlet end and an outlet end, the inlet end placed in a non-invasive adjacent position to said section and the outlet end coupled optionally to the temperature sensor means.

7. The system of claim 6 which includes an amplifier means to receive and amplify the sensing signal.

8. The system of claim 6 wherein the optical fibers range in number from about 10 to 100 optical fibers.

9. The system of claim 5 which includes a computerized electronic control means to receive the sensing signal and to monitor and control the temperature of the heated fluid in the apparatus.

10. The system of claim 1 wherein the infrared sensor means has an infrared band width of about 1–4 microns.

11. The system of claim 1 wherein the temperature sensor means measures temperature in the range of from about 30° to 300° C.

12. The system of claim 6 wherein the optical fibers comprise zirconium fluoride glass.

13. The system of claim 6 wherein the said exterior surface of the transparent section is non-linear and the optical fiber means to collect and transmit at the one end has an angle of acceptance to place the one end in substantial contact with the non-linear exterior surface of said section.

14. A system for the temperature measurement of a heat-sensitive, biological fluid in a heating apparatus, which system comprises:
 a) a heating apparatus for the heating of a fluid and which includes a microwave heating guide means to provide a microwave energy field to heat the fluid and an infrared transparent coiled tube in the energy field and having an inlet for the introduction of the fluid to be heated by the microwave guide means and the withdrawal of a heated fluid;
 b) an infrared temperature sensor means which comprises:
  i) optical fiber means to collect and transmit infrared energy from the infrared energy of the heated fluid and comprising a plurality of optical glass fibers within an outer cable, with one end and other end, with one end positioned non-invasively adjacent to the exterior surface of the said tube;
  ii) an infrared sensor means to receive from the other end the collected and transmitted infrared energy from the heated fluid in said tube to provide a sensing signal; and
  iii) means to receive and convert the sensing signal to a measure of the temperature of the heated fluid;
 c) an amplifier means to receive and amplify the sensing signal; and
 d) a computerized electronic control means to receive the sensing signal and to monitor the temperature of the heated fluid in the heating apparatus.

15. A method for the non-invasive, remote measurement of the temperature of a heated fluid, which method comprises:
 a) passing a fluid having a temperature of greater than about 30° C. through a section of an infrared, transparent material having an interior surface and an exterior surface;
 b) placing one end of an optical fiber means non-invasively adjacent the exterior surface of the transparent material in an infrared energy receiving position;
 c) collecting and transmitting the infrared energy from the heated fluid through the optical fiber means from the one to other end;
 d) providing an infrared temperature sensor means to receive the collected and transmitted infrared energy at the other end to generate a sensing signal; and
 e) receiving and converting the sensing signal into a temperature measurement for the heated fluid.

16. The method of claim 15 which includes heating and circulating a heated liquid within a tubular coil of infrared transparent material and measuring the temperature of the heated fluid at the entrance and outlet of the tubular coil.

17. The method of claim 16 which includes heating a heat-sensitive biological liquid in the tubular coil by a microwave energy field.

18. The method of claim 16 which includes heating the liquid to a selected temperature above about 60° C. for a selected heating time, holding the liquid at that temperature for a selected holding time, and cooling the liquid to below about 40° C. for a selected cooling time; the heating, holding and cooling times generally less than one second in total time, and measuring the temperature of the heated fluid at the one and other end of the tube.

19. The method of claim 15 wherein the fluid comprises a heat-sensitive biological fluid.

20. The method of claim 15 which includes passing the fluid through a coil of a transparent polymer tube.

21. The method of claim 15 which includes amplifying the sensing signal, and monitoring and controlling the temperature of the fluid responsive to the temperature measurement.

* * * * *